(12) United States Patent
Meyenhofer et al.

(10) Patent No.: US 9,301,852 B2
(45) Date of Patent: Apr. 5, 2016

(54) INSTRUMENT FOR ENGAGING AN ENGAGING MEANS ON AN IMPLANT

(75) Inventors: Andreas Meyenhofer, Schlattingen (CH); Christian Gugler, Frauenfeld (CH)

(73) Assignee: Jossi Holding AG, Islikon (CH)

( * ) Notice: Subject to any disclaimer, the term of this patent is extended or adjusted under 35 U.S.C. 154(b) by 112 days.

(21) Appl. No.: 14/115,548

(22) PCT Filed: Apr. 23, 2012

(86) PCT No.: PCT/EP2012/057397
§ 371 (c)(1),
(2), (4) Date: Nov. 4, 2013

(87) PCT Pub. No.: WO2012/150145
PCT Pub. Date: Nov. 8, 2012

(65) Prior Publication Data
US 2014/0074248 A1    Mar. 13, 2014

(30) Foreign Application Priority Data
May 4, 2011 (EP) .................................... 11164736

(51) Int. Cl.
*A61F 2/46* (2006.01)
*A61F 2/30* (2006.01)

(52) U.S. Cl.
CPC ............. *A61F 2/4609* (2013.01); *A61F 2/4637* (2013.01); *A61F 2002/30299* (2013.01); *A61F 2002/30561* (2013.01); *A61F 2002/4641* (2013.01)

(58) Field of Classification Search
CPC ........... A61F 2/4609; A61F 2002/4622; A61F 2002/4627
See application file for complete search history.

(56) References Cited

U.S. PATENT DOCUMENTS

| 2,549,731 | A | * | 4/1951 | Wattley ......................... 439/482 |
| 4,263,903 | A | | 4/1981 | Griggs |
| 4,305,394 | A | | 12/1981 | Bertuch |
| 5,116,339 | A | | 5/1992 | Glock |
| 5,370,702 | A | | 12/1994 | Jones |
| 6,626,913 | B1 | | 9/2003 | McKinnon et al. |
| 9,028,553 | B2 | * | 5/2015 | Lindenmann et al. ..... 623/17.16 |

FOREIGN PATENT DOCUMENTS

| DE | 102008022329 | 11/2009 |
| EP | 940203 | 9/1999 |
| FR | 2838329 | 10/2003 |
| WO | 2004/010882 | 2/2004 |

* cited by examiner

*Primary Examiner* — Andrew Yang
(74) *Attorney, Agent, or Firm* — Davis & Bujold PLLC; Michael J. Bujold

(57) ABSTRACT

The instrument has a collet (19) that has at least two clamping jaws (18, 18') for engaging an engaging means (4) on an implant body (1). The collet is received in a sleeve portion (20), the free end (21) of which has a support portion (22) that can be supported on the surface of the implant. A tension element (23) that engages the collet is used as an actuating means for actuating the collet. The outer faces of the clamping jaws interact with the inner face of the sleeve portion such that the collet can be closed and moved relative to the free end of the sleeve portion by pulling the tension element.

18 Claims, 9 Drawing Sheets

Figure 1:
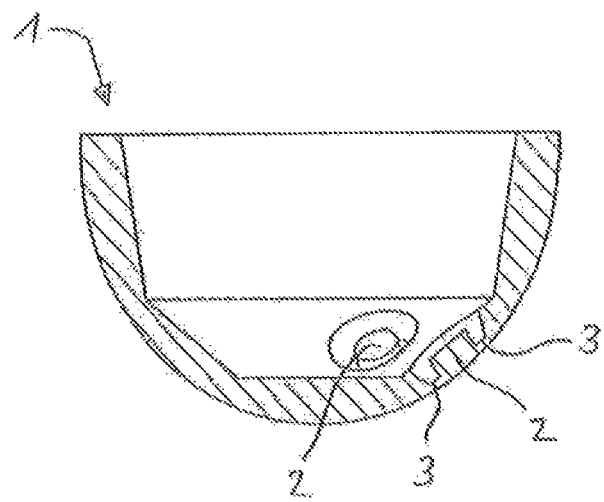

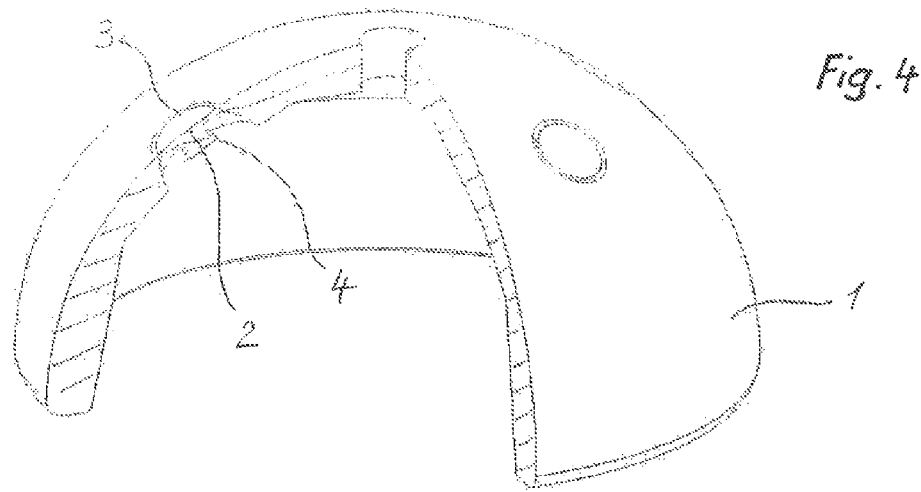
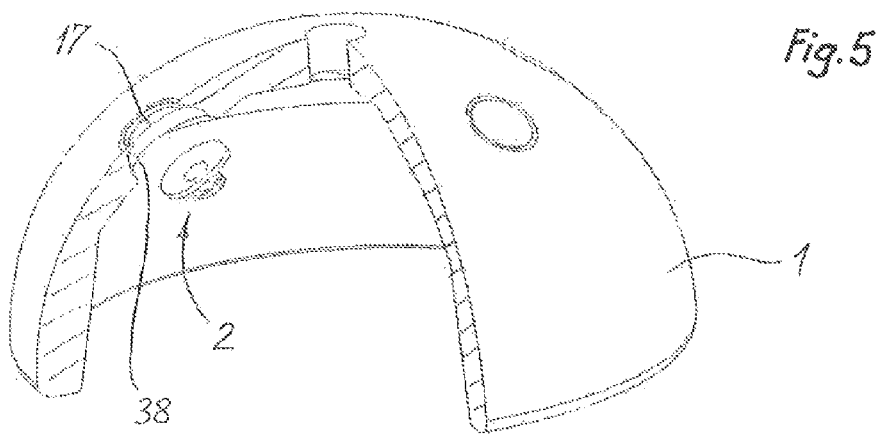
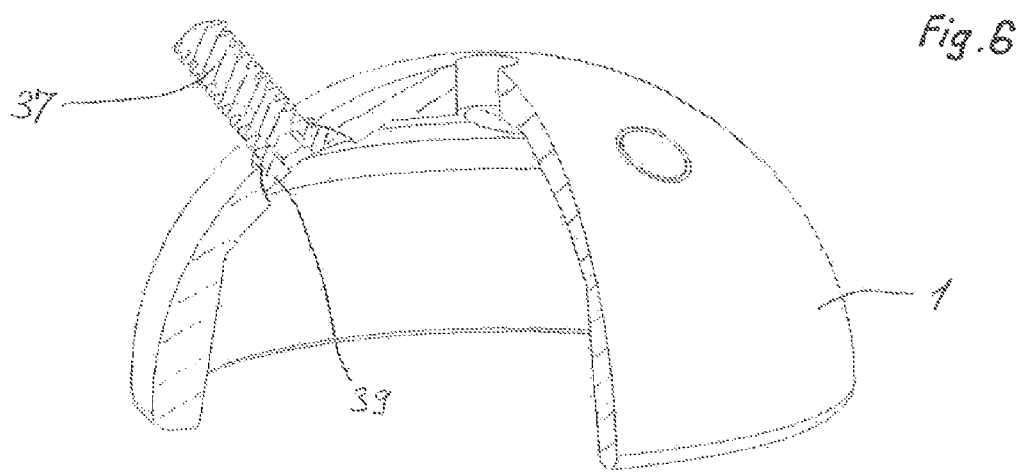

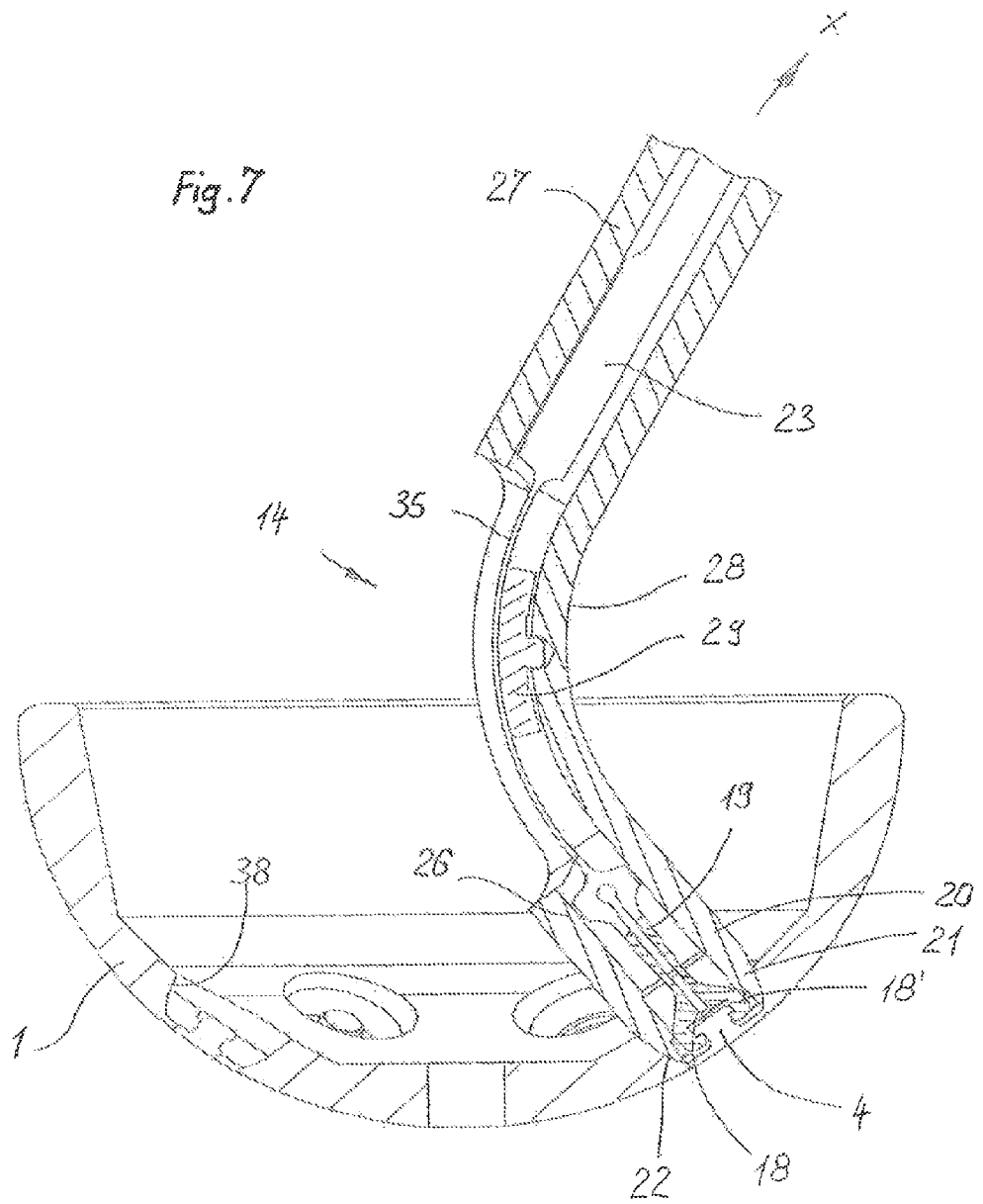

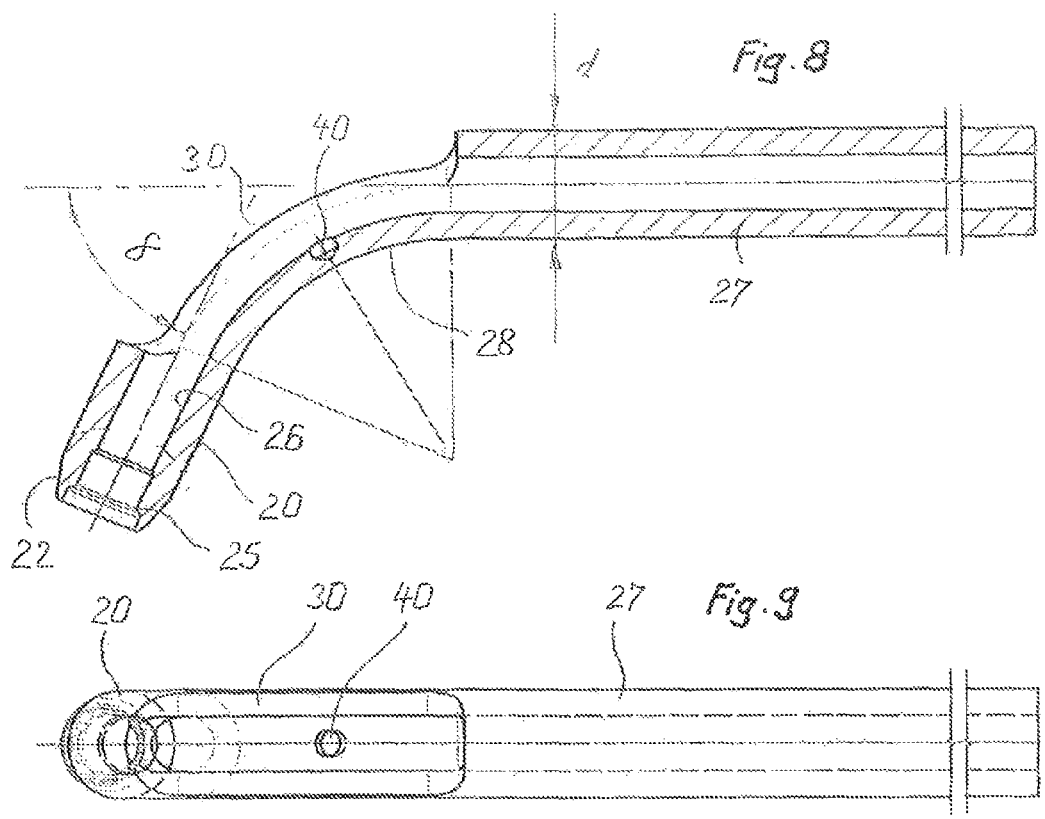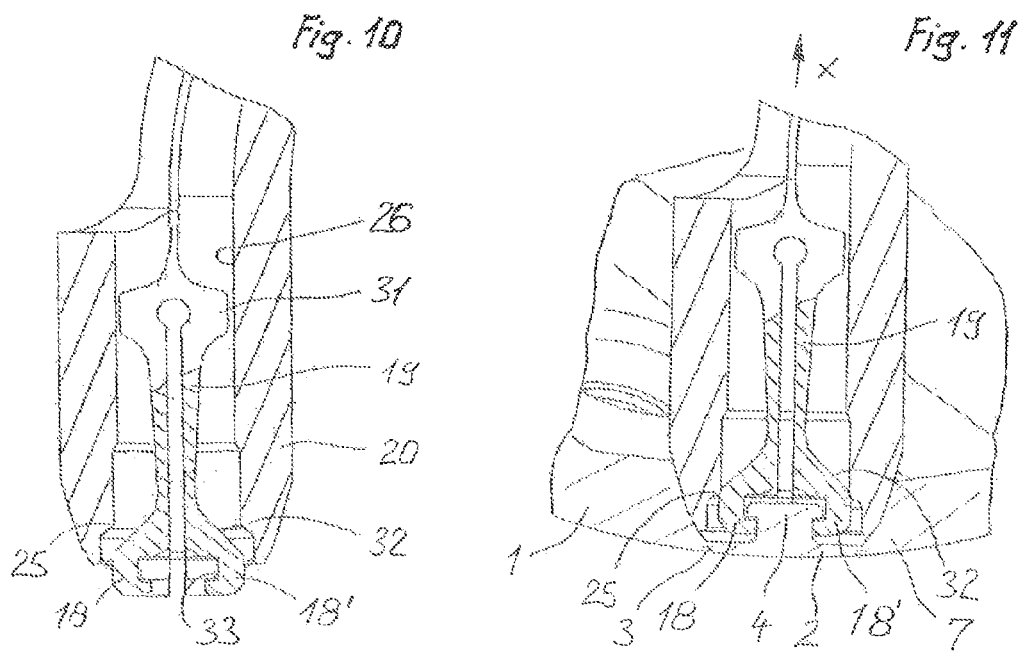

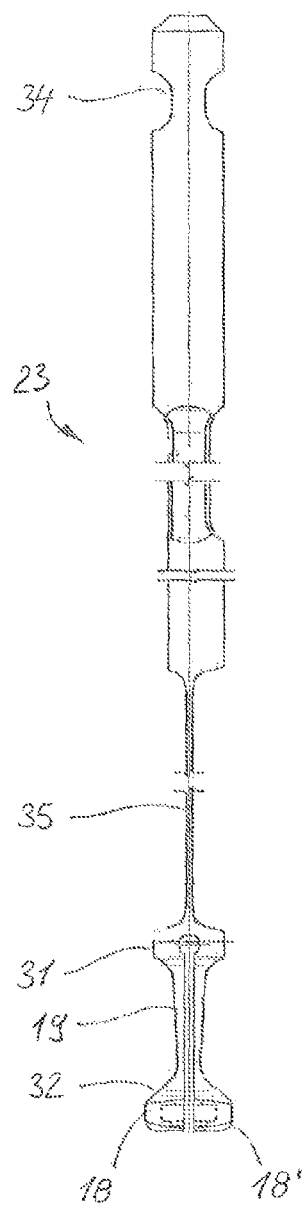
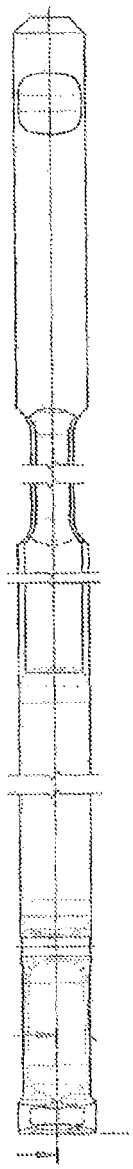
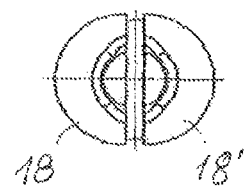
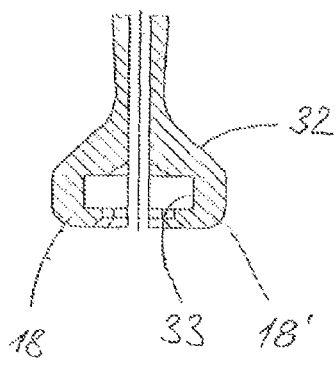

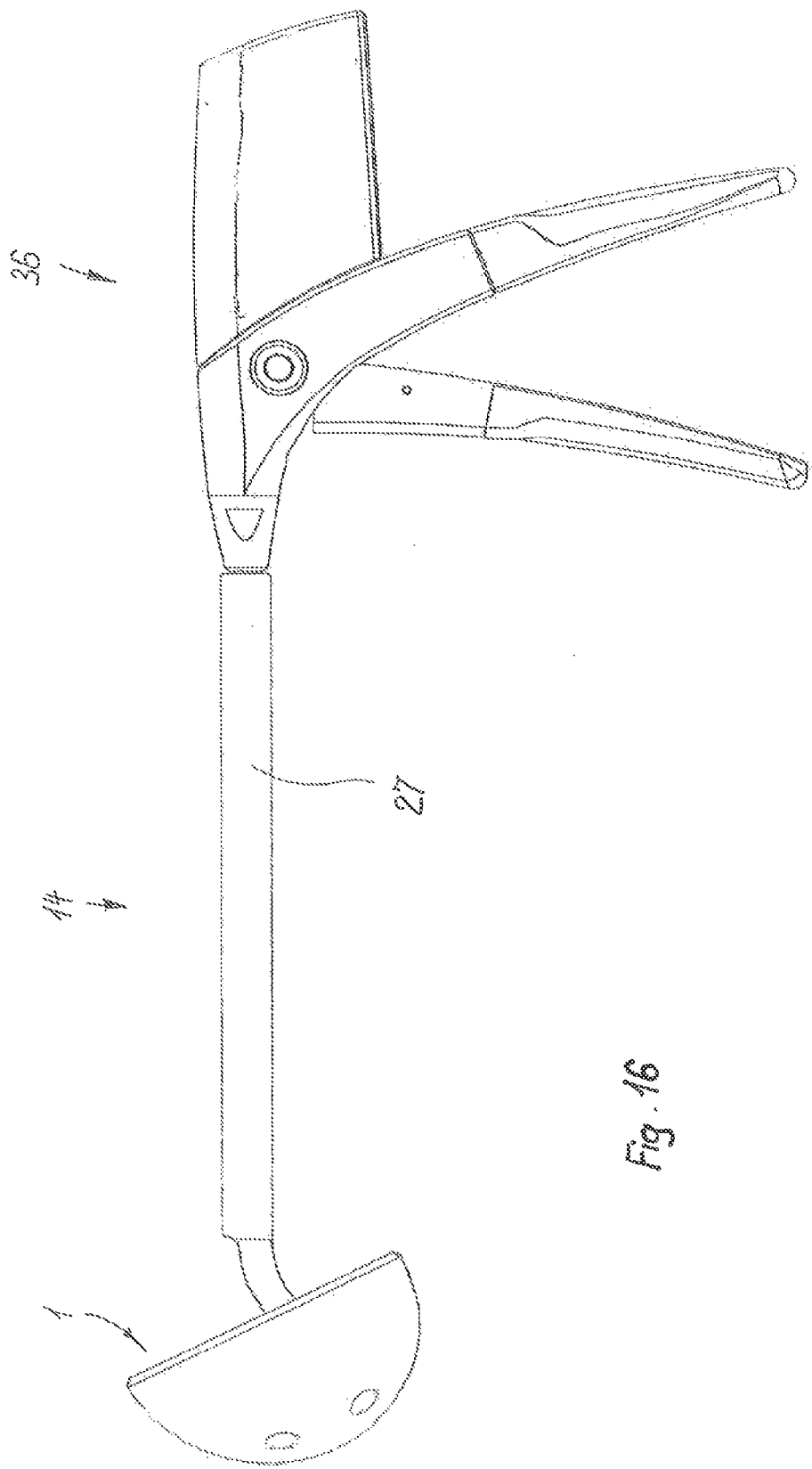

INSTRUMENT FOR ENGAGING AN ENGAGING MEANS ON AN IMPLANT

The invention relates to an instrument for gripping an engagement means on an implant, as per the preamble of claim 1. Such instruments are used for example for freeing an opening on a hip joint socket. The instruments may however also serve merely for handling the implant itself.

U.S. Pat. No. 5,370,702 has disclosed a hip joint socket, on which so-called screw funnel closures can optionally be broken out. The closure portions, which are formed in one piece with the socket, are provided with inwardly projecting pegs which serve as engagement means for a tool. By means of said tool, tensile or bending forces can be exerted on the closure portion until said closure portion can, in the region of an encircling weakened zone, be detached from the socket. A tool suitable for this purpose is however not described.

U.S. Pat. No. 4,263,903 describes an apparatus for holding medical staples. Said device has a collet by means of which the U-shaped staples can be gripped. The collet is preloaded into an open position and can be closed by linear displacement in the interior of a sleeve. As a tension element for the displacement of the collet, use is made of a threaded nut, the rotation of which causes a threaded bolt to be displaced. Said instrument is not suitable for gripping an implant, and in particular, is also not suitable for freeing the above-described screw funnel closures.

DE 10 2008 022 329 describes a handling system for a hip joint socket. The instrument likewise has a collet which can grip a central bolt on the hip joint socket. The instrument also has a sleeve portion, the end side of which can be supported on a corresponding support surface. A bracing action between the collet and implant is attained in this way. The collet is actuated indirectly via a clamping sleeve, which necessitates a relatively complex construction. Furthermore, said instrument is not suitable for breaking out screw funnel closures.

U.S. Pat. No. 6,626,913 describes an instrument for inserting implants, which instrument has a frame with a central bore. In said bore, there is guided a tension rod which is subjected to spring preload and whose end can be connected to the implant. The tension rod can be actuated by means of a lever articulatedly connected laterally to the frame. Said instrument is also not suitable for breaking out screw funnel closures, and furthermore, said instrument is difficult to handle owing to the frame being designed to be open on both sides.

It is therefore an object of the invention to provide an instrument of the type mentioned in the introduction, which instrument is of simple construction and, at the same time, can be handled reliably. The instrument should make it possible for even relatively small openings to be freed, and should be actuable with little exertion of force. Said object is achieved according to the invention by means of an instrument which has the features in claim 1. The tension element which engages directly on the collet permits a simple and space-saving design. Here, the outer sides of the clamping jaws interact with the inner side of the sleeve portion such that, by virtue of tension being exerted on the tension element, the collet can be closed and is thus made displaceable relative to the free end of the sleeve portion. Here, the free end has a support portion which can be supported on the surface of the implant. Here, the implant serves as an abutment for accommodating the tensile forces exerted by means of the collet. In this way, no detrimental forces are exerted on an already implanted socket, and the instrument itself is also not subjected to unnecessarily high load.

It is self-evidently possible for the instrument according to the invention to also be used, in certain situations, for purposes other than breaking out screw funnel closures. In particular, the insertion, positioning or removal of an implant would also be conceivable.

The support portion is preferably of frustoconical form, thereby ensuring a secure fit. Here, the frustoconical shape preferably corresponds to the configuration of the screw funnel on a screw funnel closure.

The above-described interaction between the outer side of the clamping jaws and the inner side of the sleeve portion may advantageously be realized by virtue of the sleeve portion having, on the inner side, a tapering which interacts with outer sides of the clamping jaws. Furthermore, on the inner side of the sleeve portion, there may also be arranged at least one preferably cylindrical guide portion for guiding the collet. In this way, the sleeve portion serves for the rectilinear guidance and tensioning of the collet.

The sleeve portion may be arranged on the end of, and preferably integrally connected to, a hollow shank, wherein the tension element extends through the hollow shank. Here, the hollow shank may also be formed directly as a handle, as presented for example in U.S. Pat. No. 4,263,903. The hollow shank may however also serve merely for the guidance of the tension means.

The sleeve portion may be angled relative to the hollow shank by means of a bend. Said angled configuration makes it easier, in the case of a hip joint socket, to access screw funnel closures arranged close to the equator. This applies in particular to hip sockets that have already been implanted, and in the case of which the access through the surgical incision should not be unnecessarily enlarged. The instrument is therefore highly suitable for the minimally invasive operating techniques that are common nowadays. The bend may self-evidently be adapted to the respective conditions of the individual implant and/or to the operating techniques. The angle may for example be approximately 60°.

Further advantages can be attained if, in the inner region of the bend, there is arranged a sliding block with a curved sliding surface for the diversion of the tension element. Depending on the material pairing, it is possible by means of the sliding block for friction to be greatly reduced. This is particularly important because, as is clear, the use of lubricants on surgical instruments is not admissible. A reduction in friction may additionally or alternatively also be realized through a particular configuration of the bend, by virtue of the bend, at least in the region in which sliding friction against the tension element arises, running not as a segment of a circle but rather being flattened from the apex of the bend toward the straight portions. The curvature could for example be in the form of a double involute, double clothoid or some other suitable curved form.

Since such instruments must be cleaned and sterilized in suitable apparatuses, it is particularly expedient if, in the outer region of the bend, there is arranged an opening which extends preferably over the entire bend. By means of said opening, it is ensured that cleaning fluid and sterilization agent can reach all regions of the interior wall.

A particularly simple design is attained if the clamping jaws of the collet are integrally connected to one another at a guide portion. The clamping jaws move relative to one another exclusively owing to inherent resilience of the material, such that no additional mechanical parts are necessary. The collet can thereby also be cleaned and sterilized more easily. The clamping jaws may have, on the outer side and at a distance from the guide portion, a clamping ramp portion which interacts with the inner side of the sleeve portion. The distance between the guide portion and the clamping ramp portion thus defines a lever arm about which the clamping jaws move toward one another.

For particularly secure attachment of the clamping jaws, these may have, on the inner side, an undercut for gripping a projection on the engagement means of the implant. With corresponding configuration, the engagement means can no longer be removed from the closed clamping jaws. Alternatively, the clamping jaws could self-evidently also have, on the inner side, ribs or pegs for improved grip on the engagement means.

The tension element is advantageously in the form of a tension rod which is guided at least in sections in the hollow shank. With the tension rod, it is possible for forces to be transmitted in both directions in the tension element without problems. Alternatively, the tension element could self-evidently also be in the form of a Bowden cable. The tension rod or else the Bowden cable may have a mounting portion for mounting in a tension apparatus. In this way, the tension apparatus itself can be separated from the tension element, or the tension element may be coupled to different tension apparatuses.

In particular in the case of a curved profile of the tension element, it is expedient for said tension element to be, at least in sections, of flexible form, preferably in the form of a leaf spring. A leaf spring can bend relatively easily about an axis running parallel to the wide side, and it is likewise possible for thrust forces and tensile forces to be transmitted by means of a leaf spring of said type.

The production and cleaning of the instrument may be further simplified by virtue of the collet being formed integrally with the tension element. The instrument is thereby composed, aside from the tension apparatus itself, of only two constituent parts, specifically the hollow shank with integrally formed sleeve portion, and the collet with integrally formed tension element.

A high level of operational reliability, in particular during the handling of the instrument during an operation on a patient, can be achieved if the sleeve portion and the tension element are connected directly or indirectly and in a releasable manner to a tension apparatus, at which a tension force that has been built up can be maintained such that the closed collet opens only after the release of a locking mechanism. In this way, a situation is prevented in which, after the detachment of a closure portion, the collet inadvertently opens and the portion is thus able to pass into the area of operation. Only after the deliberate and intentional release of the locking mechanism can the broken-out closure portion be removed from the collet and disposed of. This function is self-evidently expedient even if the instrument is not used in vivo.

It has proven to be particularly advantageous for the tension apparatus to be a preferably manually operated blind rivet tool, or for the tension apparatus to be able to perform the function of such a tool. As is known, said tools are capable of gripping the pin of a blind rivet and pulling said pin into the tool, wherein a defined tensile force can be imparted. Furthermore, such tools also have a locking mechanism for releasing the broken-off rivet pin and for restoring the initial position for gripping a new pin. These properties can be used in an ideal manner for actuating the tension apparatus on the instrument according to the invention, wherein adaptations for use in the medical field are self-evidently required. The invention thus also relates to the use of a preferably manually operated blind rivet tool as a tension apparatus for the actuation of an instrument for gripping an engagement means on an implant. Other force generators are however conceivable as tension apparatuses. Said force generators may be operable manually, by electric motor or pneumatically.

Finally, the invention also relates to an arrangement composed of an implant and of an instrument, having the features in claim 16.

In a further advantageous refinement within the context of the present invention, an instrument has an elongate handle and engaging means. The engaging means can be connected in a releasable manner to the closure portion.

The elongate handle can be used to apply a force for removing the closure portion from the wall of the implant. Here, the engaging means serve to transfer the force from the handle to the closure portion, and the closure portion can thus be removed safely and easily from the implant wall.

The engaging means are preferably designed such that they can be connected to an engagement means arranged on the closure portion. In this way, the closure portion can be connected captively to the instrument, which also permits removal of a closure portion in the case of an already-inserted implant.

A closure portion according to the invention may also be removed by being subjected to pressure forces or tensile forces. This can be performed, for example, by pressing or striking and by pulling. Alternatively, a closure portion according to the invention may also be removed by bending or turning forces.

Figure 2:
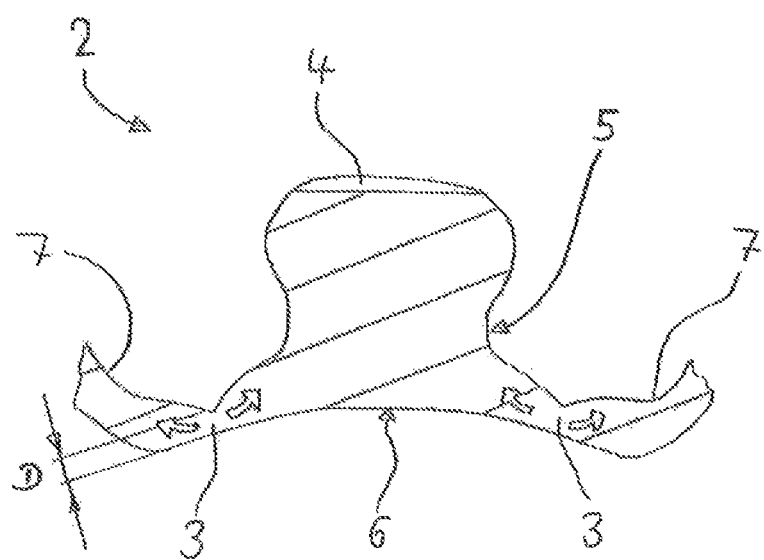
Figure 17:
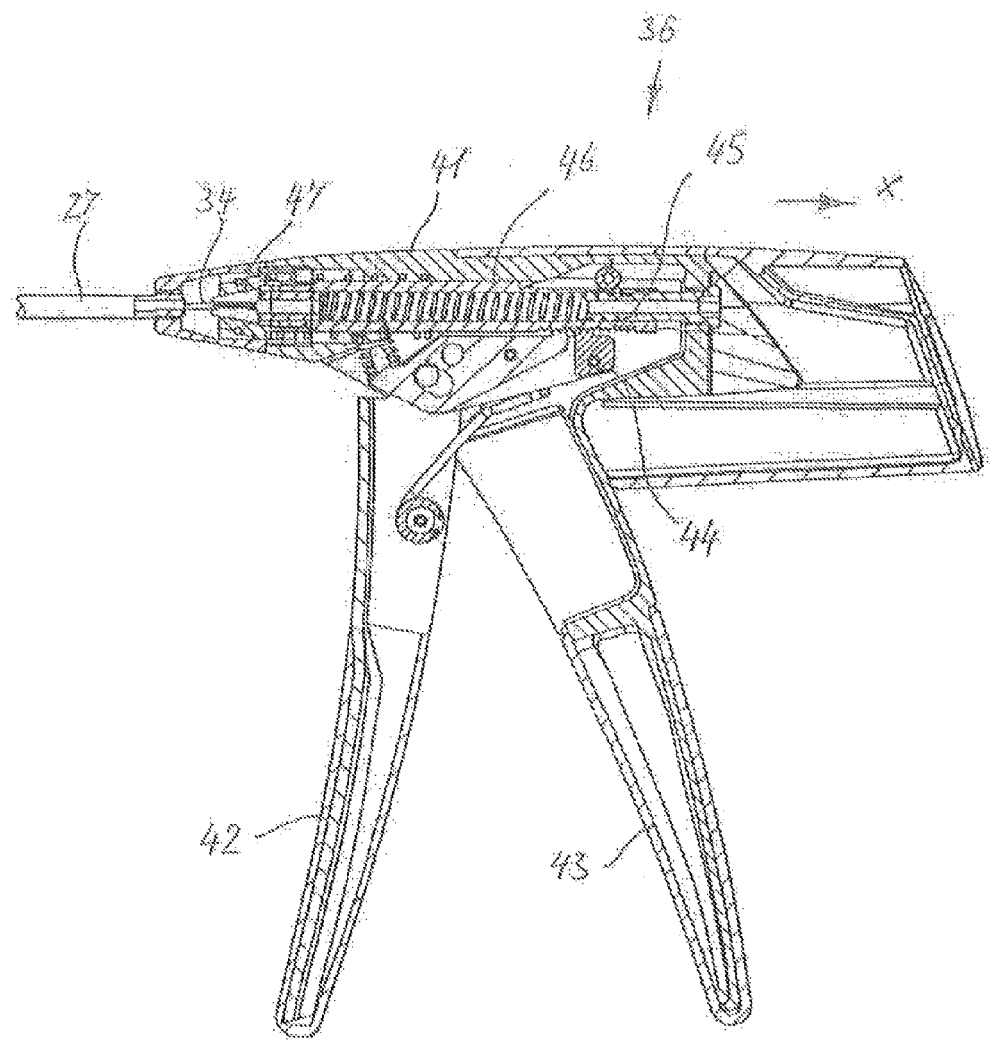
Figure 18:
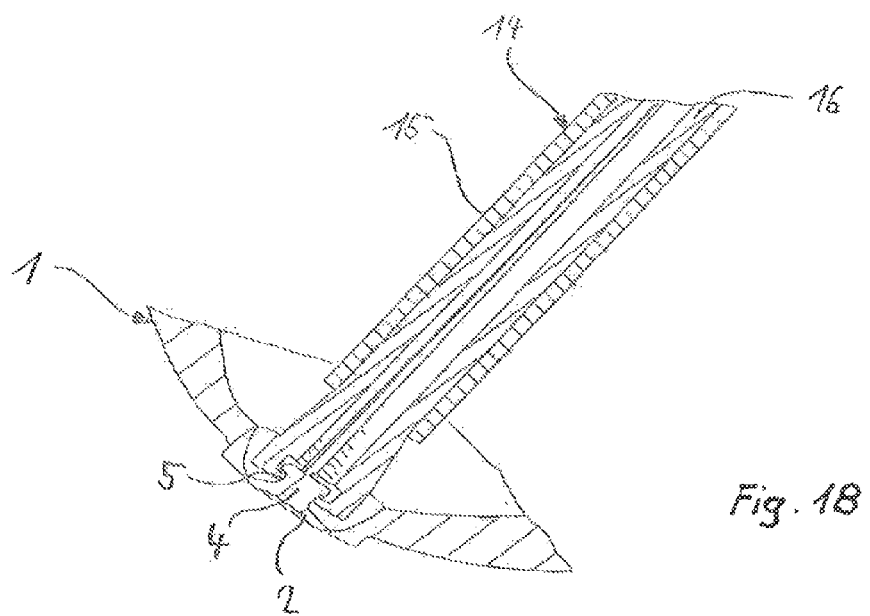

Advantages and individual features of the invention will be described in more detail below and illustrated in the drawings, in which:

FIG. 1 shows a schematic cross section through an implant,

FIG. 2 shows a cross section through a closure portion with a predetermined break line, in a greatly enlarged view, FIGS. 3a-3e show five different schematic cross sections through removable closure portions with predetermined break lines, FIG. 4 shows a perspective and partially cut-away illustration of a hip joint socket with multiple closure portions, FIG. 5 shows the hip joint socket as per FIG. 4 with a detached closure portion, FIG. 6 shows the hip joint socket as per FIG. 5 with a screw inserted into the freed opening, FIG. 7 shows a partial cross section through an instrument according to the invention during the gripping of a closure portion, FIG. 8 shows a partial cross section through a hollow shank with angled sleeve portion, FIG. 9 shows a plan view of the hollow shank as per FIG. 8 in the region of the bend, FIG. 10 shows a cross section through a sleeve portion with collet before attachment to the implant, FIG. 11 shows the sleeve portion as per FIG. 10 in the attached state, FIG. 12 shows a side view of a collet with tension element, FIG. 13 shows the collet with tension element as per FIG. 12, rotated through 90°, FIG. 14 shows a view of the face side of the collet as per FIG. 12 on an enlarged scale, FIG. 15 shows a cross section through the collet as per FIG. 12 on an enlarged scale, FIG. 16 shows the overall illustration of an arrangement composed of implant body, instrument and tension apparatus, FIG. 17 shows a cross section through the tension apparatus as per FIG. 16, and FIG. 18 shows a cross section through a modified exemplary embodiment of an instrument.

FIG. 1 shows a schematic cross section of an implant 1 in which closure portions 2 delimited by predetermined break lines 3 have been formed by means of material deformation. The implant 1 is configured by way of example as a hip joint socket. Alternatively, however, the implant may also be some other implant, for example an osteosynthesis plate. The implant 1 has, for example, two closure portions 2. However, an implant 1 may also have only one closure portion 2 or more than two closure portions 2. The closure portions 2 may be arranged in any desired arrangement on the surface of the implant 1.

FIG. 2 shows a schematic section through a closure portion of an implant, in which a closure portion 2 delimited by a predetermined break line 3 has been formed by means of a deformation process. Compared to the surrounding wall portion 7, the predetermined break line 3 has a smaller material thickness D. The material thickness D is typically less than 1 mm. The material flow generated by the deformation process, indicated by way of example by arrows, is preferably directed in a targeted manner into the closure portion 2. Alternatively, however, the material flow may also be directed in a targeted manner into the surrounding wall portion. The closure portion 2 has an engagement means 4 which, in this example, is designed as a material projection with undercut 5. Alternatively, the engagement means 4 may also have other shapes, such as for example the shape of a cylinder or of a truncated cone. The closure portion 2 additionally has a concave arch 6. The arch 6 may alternatively also be convex or undulating. The closure portion 2 may alternatively also be flat.

Figure 3A:
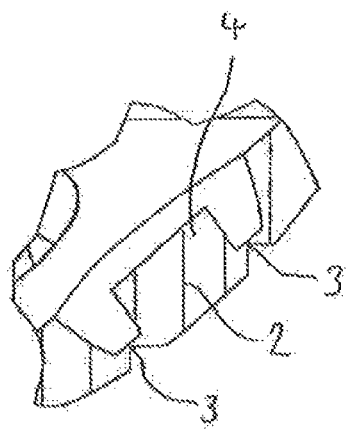
Figure 3B:
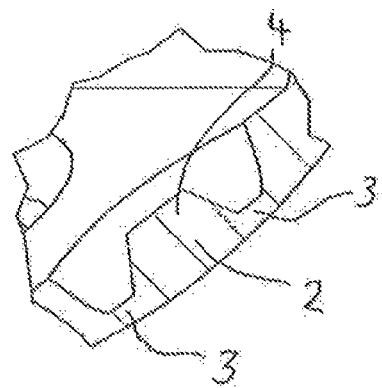
Figure 3C:
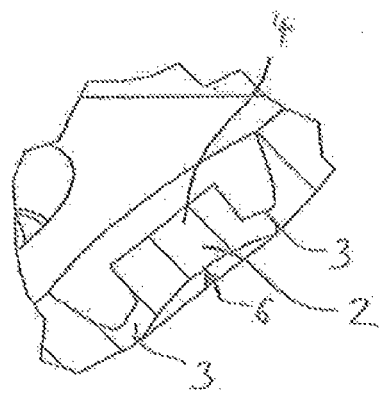
Figure 3D:
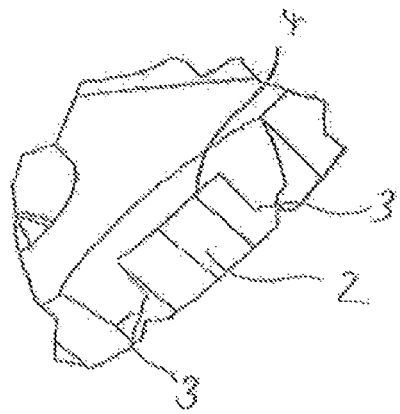
Figure 3E:
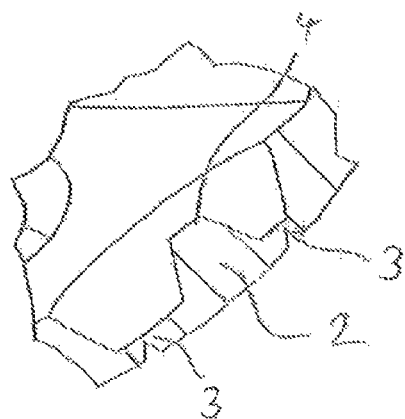

FIGS. 3a to 3e show different embodiments of closure portions 2 of an implant. Here, the embodiment in FIG. 3a has an engagement means 4 with a cylindrical or prismatic configuration. FIG. 3b shows an embodiment with a frustoconical engagement means 4. In this embodiment, the predetermined break line 3, which delimits the closure portion 2, has a greater material thickness than the embodiment in FIG. 3a. Another variant is shown in FIG. 3c. In this variant, the outside of the closure portion 4 has a convex arch 6. The closure portion 2 shown in FIG. 3a may be an intermediate step in the production of the closure portion 2 in FIG. 3c. FIG. 3d shows another embodiment of a closure portion 2 in which the material thickness of the predetermined break line 3 has been reduced on both sides of the wall of the implant. FIG. 3e shows another embodiment of a closure portion 3. In this embodiment, the engagement means 4 is not arranged centrally and symmetrically on the closure portion 2, but eccentrically. The individual features of the described embodiments of the closure portion 2 may be combined with one another as required. Different embodiments of a closure portion 2 can also be present on the same implant. As an alternative to a screw, use may also be made of other elements, such as for example nails or pins, or the opening may be used for special surgical procedures.

FIGS. 4 to 6 show an alternative exemplary embodiment of an implant body 1 in the form of a hip joint socket. In addition to the central opening in the pole region, the shell also has integrally formed therein multiple closure portions 2 which, for example analogously to the illustration in FIG. 2, are delimited by a predetermined break point 3, and which have in each case one inwardly projecting engagement means 4. The closure portions can be selectively broken out, wherein a screw funnel 38 is freed, and an opening 17 is formed (FIG. 5). Into said opening there can be inserted a screw 37, the screw head 39 of which is of complementary form to the screw funnel 38 (FIG. 6). As an alternative to a screw, it is also possible for other elements, such as for example nails or pins, to be inserted, or the opening may be utilized for special surgical procedures. The outer side of the hip joint socket may be provided with various structures for improving adhesion.

FIG. 7 shows an instrument 14 according to the invention which, to free an opening on the implant body 1, engages by way of a collet 19 on an engagement means 4. Said collet has two clamping jaws 18, 18', and said collet is mounted in a sleeve portion 20, the free end 21 of which forms a support portion 22. Said support portion fits in a complementary manner into the tapering screw funnel 38.

The collet 19 is connected to a tension element 23 which is guided in a hollow shank 27. Said hollow shank is integrally connected to the sleeve portion 20, wherein the latter is angled relative to the hollow shank at an angle of approximately 60°. The angled configuration is realized by means of a bend 28. In the region of said bend, the tension element 23 is in the form of a leaf spring 35 which rests on a sliding block 29 which is anchored in the region of the bend 28. The collet 19 is actuated by exerting tension on the tension element 23 in the arrow direction x.

FIGS. 8 and 9 show further details of the hollow shank 27 with the integrally formed sleeve portion 20. Said hollow shank is a tube with the outer diameter d, which tube is bent with a bend 28 such that the sleeve portion 20 is deflected relative to the hollow shank by an angle α of approximately 60°. As mentioned in the introduction, the bend 28 need not run as a segment of a circular arc, and instead may open toward the straight portions. In the region of the bend, an opening 30 is arranged on the outer side, which opening extends over the entire bend and the width of which opening corresponds approximately to the outer diameter d. On the inner wall of the bent portion there is arranged a blind hole 40 in which the sliding block 29 as per FIG. 7 is anchored. Said hole could also be a through bore. In the region of the support portion 22, a tapering 25 is arranged on the inner side of the sleeve portion 20. Said tapering interacts with the outer side of the clamping jaws 18, 18', as will be described in more detail below.

FIGS. 10 and 11 show details of the collet 19 in the released and tightened states. The two clamping jaws 18, 18' of the collet 19 are integrally connected to one another in the region of a guide portion 31, such that said clamping jaws can be moved relative to one another with resilient action. The guide portion 31 on the collet interacts with the guide portion 26 on the inner side of the sleeve portion 20. On the outer sides of the clamping jaws 18, 18' there is arranged in each case one clamping ramp portion 32 which can interact with the tapering 25. Furthermore, the clamping jaws are provided in each case with an undercut 33. The two clamping jaws 18, 18' may be arranged such that, in order to grip the engagement means 4, they must initially be spread apart slightly. They may alternatively be already spread apart slightly in the rest position. FIG. 11 shows once again the situation when tension is exerted on the collet 19 in the arrow direction x, wherein, as can be seen, the closure portion 2 is likewise displaced or raised relative to the implant body 1. Since the sleeve portion 20 is supported directly in the screw funnel, the bending forces that arise up to the point of rupture of the predetermined break point 3 are accommodated by the wall portion 7 surrounding the screw funnel. In this way, as is evident, no forces can arise that could damage the implant body as a whole.

FIGS. 12 to 15 show further details of the tension element 23. As illustrated, the collet 19 is connected to the rest of the tension element 23 via a leaf spring 35. Here, the width of the leaf spring corresponds to the width of the two clamping jaws 18, 18'. That portion of the tension element 23 which is remote from the collet 19 is in the form of a tube, wherein opposite cutouts are arranged on a mounting portion 34. Said cutouts serve for the mounting of the tension element 23 in a tension apparatus. As can be seen in particular from FIG. 14, the two clamping jaws 18, 18' are formed in the manner of half-shells in the region of the undercut 33. The configuration of said clamping jaws may self-evidently be adapted individually in each case to the particular shape of the engagement means. The collet 19 may readily also have more than two clamping jaws.

FIG. 16 schematically shows an arrangement composed of an implant body 1, an instrument 14 according to the invention and a manually operable tension apparatus 36. For this purpose, the above-described hollow shank 27 is fixedly connected to the tension apparatus 36 in a suitable manner, wherein said tension apparatus is also connected to the mounting portion 34 of the tension element 23 such that, when the tension apparatus 36 is actuated, a tension force can be exerted, and the parts do not corrode.

As already mentioned in the introduction, what is particularly advantageously suitable as a tension apparatus is a mechanism such as is already known from commercially available and manually operable blind rivet tools. Such a mechanism is described in detail for example in EP 0 940 203. In FIG. 17, therefore, only the most important elements will be briefly discussed once again. Accordingly, the tension apparatus 36 has a housing 41 in which a spring-loaded tension element 46 is mounted. The above-mentioned hollow shank 27 of the instrument according to the invention can be fixedly coupled to the housing 41. The tension element 46 is provided with a coupling 47 which can engage on the mounting portion 34. The device also has a handle lever 43, which is rigidly connected to the housing 41, and a pivotably mounted lever 42. The lever 42 is articulatedly connected to a tensioning lever 44, which in turn can interact via a toothing 45 with the tension element 46. The tensioning lever 44 is mounted and pre-loaded such that, by virtue of the pivotable lever 42 being actuated multiple times, the tension element 46 is moved in the arrow direction x by means of the toothing. A lock mechanism (not illustrated in any more detail here) ensures that, after each lever movement, the tension element 46 remains in the position that has already been attained. To release the lock mechanism, and thus to release the collet on the instrument, the movable lever 42 must be spread apart from the fixed lever 43, wherein for this purpose a locking force must be overcome.

The mechanism must self-evidently be adapted to the special requirements for surgical instruments. The storage container provided in the case of blind rivet tools for receiving the torn-off rivet pins may be dispensed with. Furthermore, the materials and components must be selected such that the tension apparatus can be easily cleaned and sterilized, and the parts do not corrode.

FIG. 18 shows, in section, an alternative exemplary embodiment of an instrument 14 according to the invention, which is releasably connected to a closure portion 2. The instrument 14 comprises an elongate handle 15 and engaging means 16. In the illustrated embodiment of the instrument 14, the engaging means 16 is composed of an elongate hollow body with at least the same cross section as the engagement means. At least in the region of engaging means 16, the handle 15 is likewise in the form of a hollow body which is arranged so as to be displaceable over the engaging means 16. In the example illustrated, the engaging means 16 is divided in said region into three parts that are separated from one another by tapering slots. By sliding the handle 15 over the engaging means 16, the cross section of said engaging means is narrowed, or the three parts are pushed concentrically toward one another. In this way, the engaging means 16 can engage on the engagement means. The engaging means 16 preferably has additional means that can engage into the undercut 5 of the engagement means 4.

As is evident, the handle 15 of said exemplary embodiment corresponds to the sleeve portion 20 of the exemplary embodiment described above, and the slotted engaging means 16 forms the collet. In the position illustrated, the handle 15 is not yet supported on the implant body 1. The relative displacement between the handle 15 and the engaging means 16 may be realized in any desired manner.

The invention claimed is:

1. An instrument for gripping an engagement means on an implant, having a collet which has at least two clamping jaws and which serves for gripping the engagement means, and having a sleeve portion for receiving the collet, the free end of said sleeve portion has a support portion that can be supported on the surface of the implant, further having actuation means for actuating the collet,
   wherein said actuation means has a tension element that engages on the collet, and the outer sides of the clamping jaws interact with the inner side of the sleeve portion such that, by virtue of tension being exerted on said tension element, the collet can be closed and is thus made displaceable relative to the free end of said sleeve portion,
   the sleeve portion is arranged on the end of a hollow shank, the tension element extends throughout the hollow shank, the sleeve portion is angled relative to the hollow shank by a bend, and
   there is arranged, in the inner region of the bend, a sliding block with a curved sliding surface for the diversion of the tension element.

2. The instrument as claimed in claim 1, wherein the support portion is of frustoconical form.

3. The instrument as claimed in claim 1, wherein the sleeve portion has, on the inner side, a tapering which interacts with outer sides of the clamping jaws, and in that, on the inner side, there is also arranged at least one guide portion for guiding the collet.

4. The instrument as claimed in claim 3, wherein the guide portion for guiding the collet is cylindrical.

5. The instrument as claimed in claim 1, wherein the sleeve portion is integrally connected to the hollow shank.

6. The instrument as claimed in claim 1, wherein, in the outer region of the bend, there is arranged an opening.

7. The instrument as claimed in claim 6, wherein the tension rod has a mounting portion for mounting in a tension apparatus.

8. The instrument as claimed in claim 1, wherein the clamping jaws of the collet are integrally connected to one another at a guide portion, and in that said clamping jaws have, on the outer side and at a distance from the guide portion, a clamping ramp portion which interacts with the inner side of the sleeve portion.

9. The instrument as claimed in claim 1, wherein the clamping jaws have, on their inner side, an undercut for gripping a projection on the engagement means of the implant.

10. The instrument as claimed in claim 9, wherein the flexible form of the tension element is in the form of a leaf spring.

11. The instrument as claimed in claim 1, wherein the tension element is in the form of a tension rod which is guided at least in sections in the hollow shank.

12. The instrument as claimed in claim 1, wherein the tension element is, at least in sections, of flexible form.

13. The instrument as claimed in claim 12, wherein the tension apparatus is a blind rivet tool.

14. The instrument as claimed in claim 1, wherein the collet is formed integrally with the tension element.

15. The instrument as claimed in claim 1, wherein the sleeve portion and the tension element are connected directly or indirectly and in a releasable manner to a tension apparatus, at which a tension force that has been built up can be maintained such that the closed collet opens only after the release of a locking mechanism.

16. The instrument as claimed in claim 15, wherein the at least one engagement means comprises a material projection with an undercut for the fitting of an instrument.

17. An arrangement composed of an implant with at least one wall portion which has at least one predetermined break point produced by material deformation, said predetermined break point, to free an opening or cutout, delimits a closure portion that can be removed from the wall portion under the action of force, wherein said closure portion has at least one engagement means, and of an instrument for releasably gripping said engagement means, the instrument having a collet which has at least two clamping jaws and which serves for gripping the engagement means, and having a sleeve portion for receiving the collet, the free end of said sleeve portion has a support portion that can be supported on the surface of the implant, further having actuation means for actuating the collet, wherein said actuation means has a tension element that engages on the collet, and the outer sides of the clamping jaws interact with the inner side of the sleeve portion such that, by virtue of tension being exerted on said tension element, the collet can be closed and is thus made displaceable relative to the free end of said sleeve portion.

18. An instrument for gripping an engagement means on an implant, having a collet which has at least two clamping jaws and which serves for gripping the engagement means, and having a sleeve portion for receiving the collet, the free end of said sleeve portion has a support portion that can be supported on the surface of the implant, further having actuation means for actuating the collet, wherein said actuation means has a tension element that engages on the collet, and the outer sides of the clamping jaws interact with the inner side of the sleeve portion such that, by virtue of tension being exerted on said tension element, the collet can be closed and is thus made displaceable relative to the free end of said sleeve portion, the sleeve portion is arranged on the end of a hollow shank, the tension element extends through the hollow shank, the sleeve portion is angled relative to the hollow shank by a bend, and an opening is arranged in the outer region of the bend.

* * * * *